United States Patent
Hogendijk (10) Patent No.: US 7,223,253 B2
(45) Date of Patent: May 29, 2007

(54) BLOOD ASPIRATION SYSTEM AND METHODS OF USE

(75) Inventor: Michael Hogendijk, Palo Alto, CA (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 10/209,207

(22) Filed: Jul. 29, 2002

(65) Prior Publication Data
US 2004/0019310 A1    Jan. 29, 2004

(51) Int. Cl.
*A61M 37/00* (2006.01)
*A61M 5/00* (2006.01)
*A61M 1/00* (2006.01)
*A61M 29/00* (2006.01)

(52) U.S. Cl. ............... 604/6.12; 604/4.01; 604/6.1; 604/6.11; 604/6.16; 604/7; 604/9; 604/33; 606/200

(58) Field of Classification Search ............ 604/4.01, 604/5.01, 6.09, 6.11, 7–10, 264, 27, 30, 167.05, 604/33, 65–67, 131, 151, 6.1, 6.12, 6.16; 137/455; 606/159, 200
See application file for complete search history.

(56) References Cited

U.S. PATENT DOCUMENTS

| | | | |
|---|---|---|---|
| 3,965,896 A | 6/1976 | Swank | |
| 3,985,133 A * | 10/1976 | Jenkins et al. | ........... 604/67 |
| 4,518,497 A | 5/1985 | Tsuda et al. | |
| 4,898,572 A | 2/1990 | Surugue nee Lasnier et al. | |
| 4,921,478 A | 5/1990 | Solano | |
| 5,055,198 A | 10/1991 | Shettigar | |
| 5,114,400 A | 5/1992 | Lynn | |
| 5,135,492 A | 8/1992 | Melker et al. | |
| 5,215,519 A | 6/1993 | Shettigar | |
| 5,374,401 A | 12/1994 | Von Berg | |
| 5,407,425 A | 4/1995 | Werner et al. | |
| 5,549,569 A | 8/1996 | Lynn et al. | |
| 5,743,886 A | 4/1998 | Lynn et al. | |
| 5,759,160 A | 6/1998 | Neese et al. | |
| 5,833,650 A | 11/1998 | Imran | |
| 5,876,611 A | 3/1999 | Shettigar | |
| 5,954,695 A * | 9/1999 | Sims et al. | ........... 604/131 |
| 5,961,472 A | 10/1999 | Swendson et al. | |
| 5,971,948 A | 10/1999 | Pages et al. | |
| 6,059,745 A * | 5/2000 | Gelbfish | ........... 604/6.09 |
| 6,161,547 A * | 12/2000 | Barbut | ........... 128/898 |
| 6,251,291 B1 | 6/2001 | Lamphere et al. | |
| 6,423,032 B2 | 7/2002 | Parodi | |
| 6,447,473 B1 * | 9/2002 | Levine et al. | ........... 604/33 |
| 2001/0049486 A1 * | 12/2001 | Evans et al. | ........... 604/4.01 |

* cited by examiner

*Primary Examiner*—Tatyana Zalukaeva
*Assistant Examiner*—Leslie R. Deak
(74) *Attorney, Agent, or Firm*—Kevin J. Boland (57) ABSTRACT

The present invention is directed to a blood aspiration system that is configured to enable various types of aspiration through a working lumen of a catheter. The blood aspiration system facilitates natural aspiration by providing a circuit between a patient's arterial and venous vasculature, and also comprises a manually actuated pump configured to selectively vary rates of aspiration in the working lumen. The blood aspiration system further comprises an external port that allows suction-assisted aspiration or infusion through the working lumen, and further comprises a detachable filter that removes emboli prior to reperfusing blood into a patient's venous vasculature.

24 Claims, 8 Drawing Sheets

BLOOD ASPIRATION SYSTEM AND METHODS OF USE

FIELD OF THE INVENTION

The present invention relates to a blood aspiration system for use in conjunction with a catheter during a medical procedure, and more specifically, a system that is configured to provide a working lumen of the catheter with substantially continuous natural aspiration and, optionally, pump-assisted aspiration.

BACKGROUND OF THE INVENTION

Today there is a growing need to provide controlled access and vessel management during such procedures as stenting, atherectomy or angioplasty. Generally during these procedures there is a high opportunity for the release of embolic material. The emboli may travel downstream from the occlusion, lodging deep within the vascular bed and causing ischemia. The resulting ischemia may pose a serious threat to the health or life of a patient if the blockage forms in a critical area, such as the heart, lungs, or brain.

Several previously known methods and apparatus incorporate the use of an external suction system in conjunction with an aspiration catheter for removal of the clot and/or removal of embolic particles. However, several disadvantages arise when using an external suction system as the sole means for flow management within a vessel. First, it may be difficult to establish the proper aspirating pressure required at the treatment site, and external pressure adjustments used with suction pumps may lead to an incorrect amount of suction for a given set of circumstances. If the amount of suction is too low for the circumstances, then embolic particles may not be effectively removed and may travel downstream from the original occlusion, leading to further occlusive events. If the amount of suction is too high, the vessel may collapse.

Moreover, if an external suction pump is utilized, retrieval of downstream emboli may require a flow rate that cannot be sustained by the vessel wall for more than a few seconds, resulting in insufficient removal of emboli. Additionally, continuous use of an external suction pump may result in excessive blood loss, requiring infusion of non-autologous blood and raising related safety issues.

Furthermore, use of an external suction pump generally requires drawing fluid from a patient's vessel and then reintroducing the fluid back into a filter using a three-way stopcock. This cumbersome technique may cause injury to blood cells and may limit the ability of the physician while performing the procedure.

Other methods for embolic removal have relied on more natural aspirating effects. For example, previously known devices have relied on the pressure differential between the atmosphere and blood flow in a treatment vessel to cause a reversal of flow in the treatment vessel. However, such natural aspiration techniques may provide insufficient flow to effectively remove emboli.

In view of these drawbacks of previously known systems, it would be desirable to provide a blood aspiration system that allows a catheter to achieve a substantially continuous rate of natural, physiologically-regulated aspiration through a working lumen of the catheter.

It also would be desirable to provide a blood aspiration system that provides an appropriate rate of retrograde flow at a treatment site to direct dislodged particles into a catheter for efficient removal without damaging the treatment vessel.

It further would be desirable to provide a blood aspiration system having an easy to use pump that selectively may be used, in conjunction with natural aspiration techniques, to further influence flow in a treatment vessel.

It yet further would be desirable to provide a blood aspiration system that provides a suction/infusion port that optionally may be used to further influence aspiration in the catheter lumen and/or to infuse drugs or agents into the catheter lumen.

It still further would be desirable to provide a blood aspiration system that allows emboli to be filtered and blood reperfused into a patient's vessel to reduce blood loss.

SUMMARY OF THE INVENTION

In view of the foregoing, it is an object of the present invention to provide a blood aspiration system that allows a catheter to achieve a substantially continuous rate of natural, physiologically-regulated aspiration through a working lumen of the catheter.

It is also an object of the present invention to provide a blood aspiration system that provides an appropriate rate of retrograde flow at a treatment site to direct dislodged particles into a catheter for efficient removal, without damaging the treatment vessel.

It is a further object of the present invention to provide a blood aspiration system having an easy to use pump that selectively may be used, in conjunction with natural aspiration techniques, to further influence flow in a treatment vessel.

It is still a further object of the present invention to provide a blood aspiration system that provides a suction/infusion port that optionally may be used to further influence aspiration in the catheter lumen and/or to infuse drugs or agents into the catheter lumen.

It is yet a further object of the present invention to provide a blood aspiration system that allows emboli to be filtered and blood reperfused into a patient's vessel to reduce blood loss.

These and other objects of the present invention are accomplished by providing a blood aspiration system that is configured to enable three types of aspiration through a working lumen of a catheter. The blood aspiration system enables a substantially continuous rate of natural, physiologically-regulated aspiration through the working lumen using an arterial-venous shunt and, optionally, pump-assisted or suction-assisted aspiration through the catheter lumen. This allows a physician to provide a substantially continuous rate of retrograde flow in a treatment vessel during a medical procedure, while allowing a physician to further influence the rate of aspiration within the vessel.

In a preferred embodiment, the blood aspiration system of the present invention comprises a manifold having an inlet port in fluid communication with the working lumen of the catheter and an outlet port that preferably is coupled to a patient's venous vasculature. The blood aspiration system further comprises a manually actuated pump including a housing having a lumen and a plunger disposed within the lumen. The manifold further preferably comprises a plurality of valves, described hereinbelow, that are configured to channel flow through the manifold exclusively in one direction when the pump is actuated.

In operation, the outlet port preferably is coupled to a venous return sheath, which is adapted to be disposed in a remote vein. When the venous return sheath is disposed in the remote vein, and when an occlusive element of the catheter is deployed in a patient's artery, a pressure differential between venous and arterial pressure will cause blood to flow in a retrograde fashion in the artery. This natural, physiologically-regulated aspiration through the manifold preferably occurs before, during and after a medical procedure performed through the working lumen of the catheter to effectively remove thrombi and/or emboli from the vessel.

The manifold preferably comprises a slide valve disposed between the inlet port and the outlet port. The slide valve preferably comprises a block having a bore that selectively directs fluid flow between the inlet port and the outlet port when the plunger is in an advanced position. When the plunger is retracted, a spring pushes the block proximally to cause the slide valve to be in a closed position whereby natural aspiration is temporarily inhibited.

Additional aspiration selectively may be provided through the working lumen of the catheter using the pump. When the slide valve is in the closed position and natural aspiration is temporarily inhibited, the retraction of the plunger draws fluid into a pump chamber formed between a first check valve and the plunger. As fluid is drawn into the pump chamber, increased rates of aspiration within the working lumen of the catheter are provided. The physician then may distally advance the plunger to cause fluid to flow from the pump chamber, through a second check valve and into the outlet port.

If desired, suction-assisted aspiration also selectively may be applied using a suction/infusion port coupled to the manifold. Alternatively, a syringe may be coupled to suction/infusion port to infuse saline, drugs or other therapeutic agents to the treatment site.

The apparatus of the present invention further preferably comprises a detachable filter chamber coupled to the manifold. Blood exiting through the outlet port of the manifold flows into the filter chamber and through a filter, prior to being reperfused into a remote vein. The filter chamber is detachable from the manifold to allow filtered emboli to be studied and characterized.

Methods of using the apparatus of the present invention also are provided.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention is directed to a blood aspiration system that is configured to enable natural aspiration through a working lumen of a catheter and, optionally, pump-assisted aspiration through the working lumen. The blood aspiration system enables a substantially continuous rate of natural, physiologically-regulated aspiration through the working lumen by enabling fluid communication between the working lumen and a patient's venous vasculature. The blood aspiration system further comprises a manually actuated pump provided to allow increased rates of aspiration through the working lumen. The provision of substantially continuous retrograde flow and, optionally, selectively increased rates of retrograde flow at a treatment site facilitates removal of emboli during an interventional procedure while minimizing trauma to the treatment vessel.

Figure 1A:
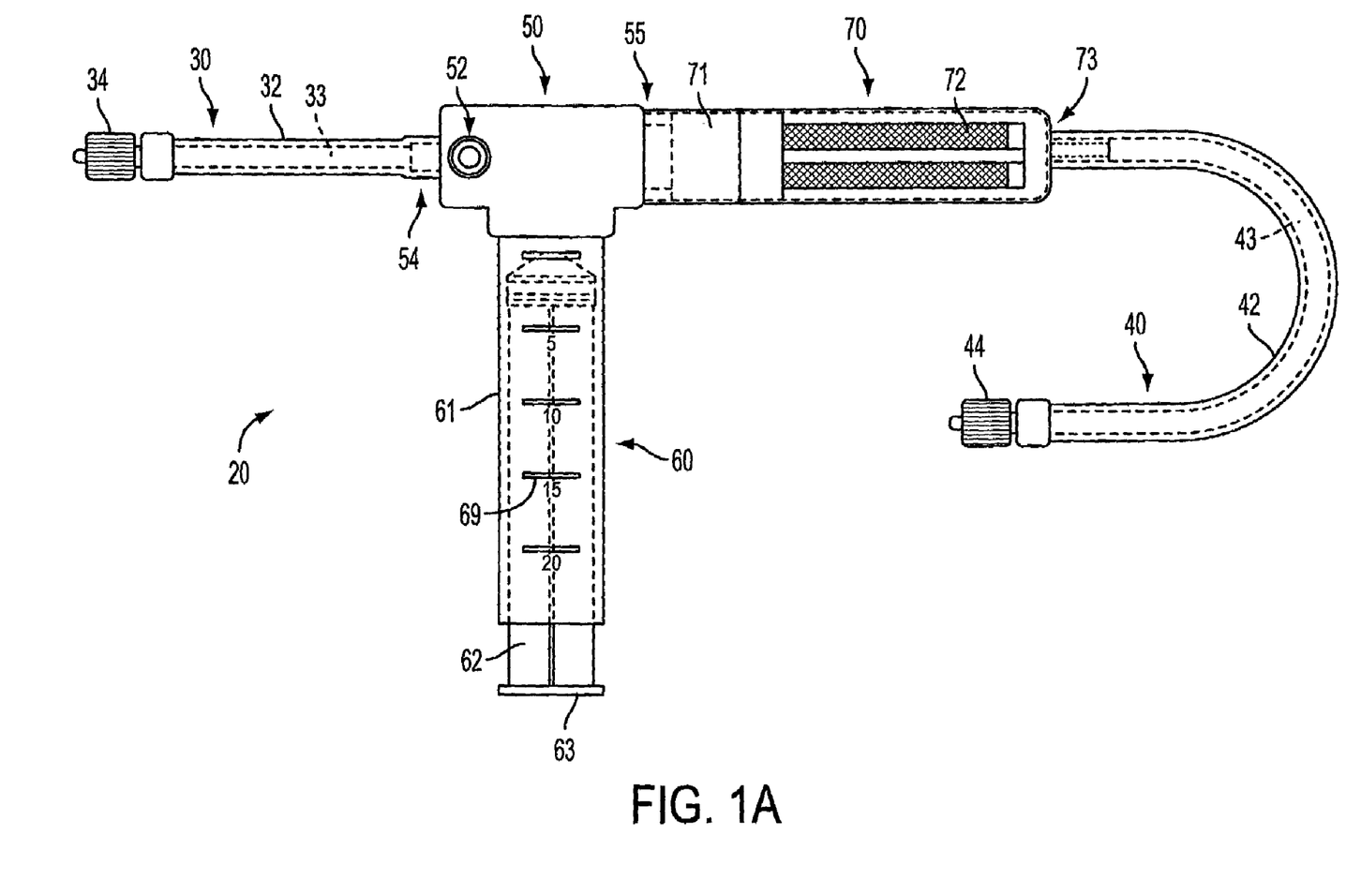
FIGS. 1A-1B provide side and side sectional views of a blood aspiration system in accordance with principles of the present invention.
Figure 1B:
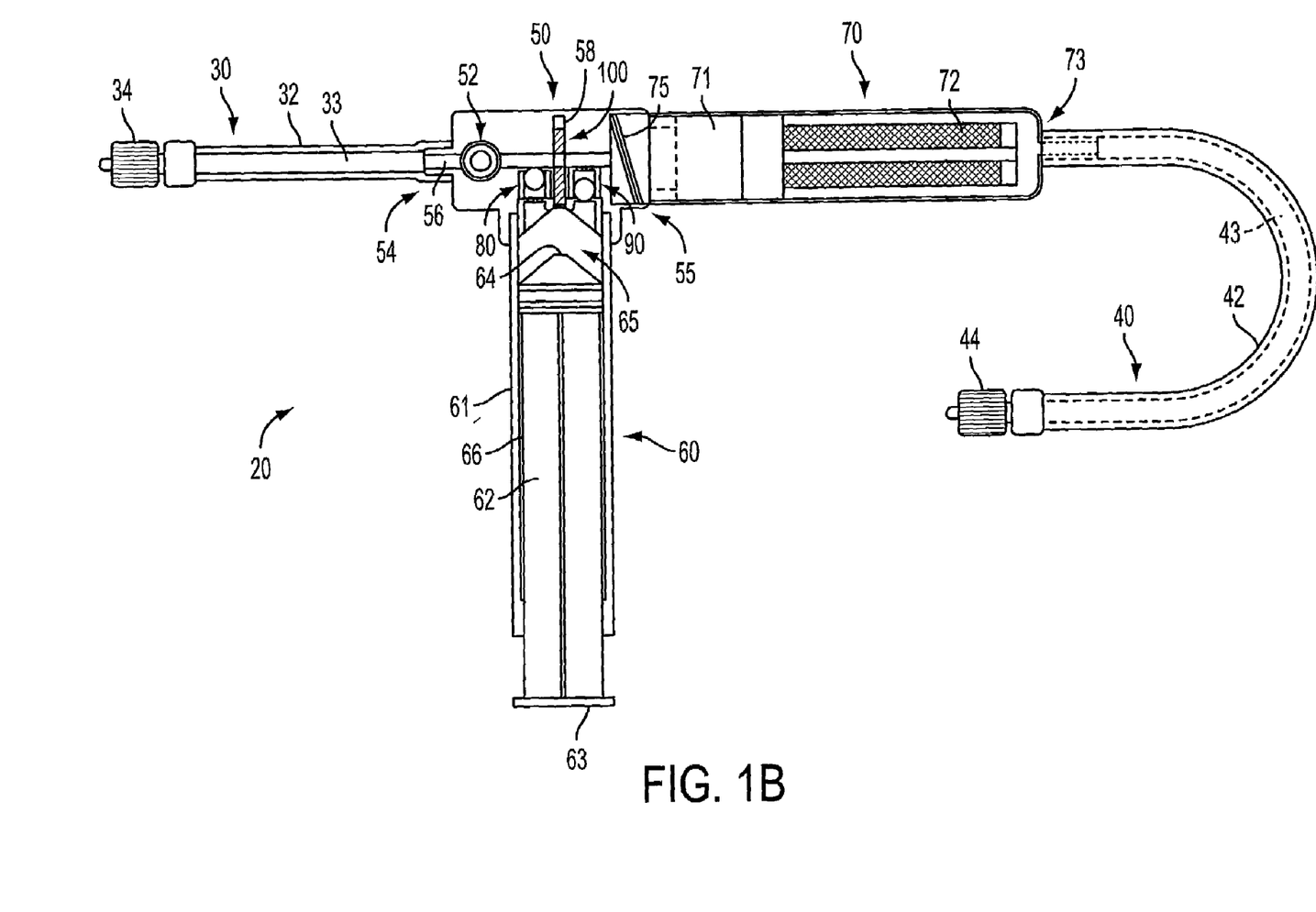

Referring now to FIG. 1, features of a blood aspiration system constructed in accordance with principles of the present invention are described. Blood aspiration system 20 preferably comprises manifold 50 having inlet port 54 and outlet port 55, and further comprises pump 60 coupled to manifold 50. Blood aspiration system 20 preferably further comprises arterial line 30, venous line 40, and filter chamber 70, which are coupled to manifold 50 and pump 60 as described hereinbelow.

Figure 2:
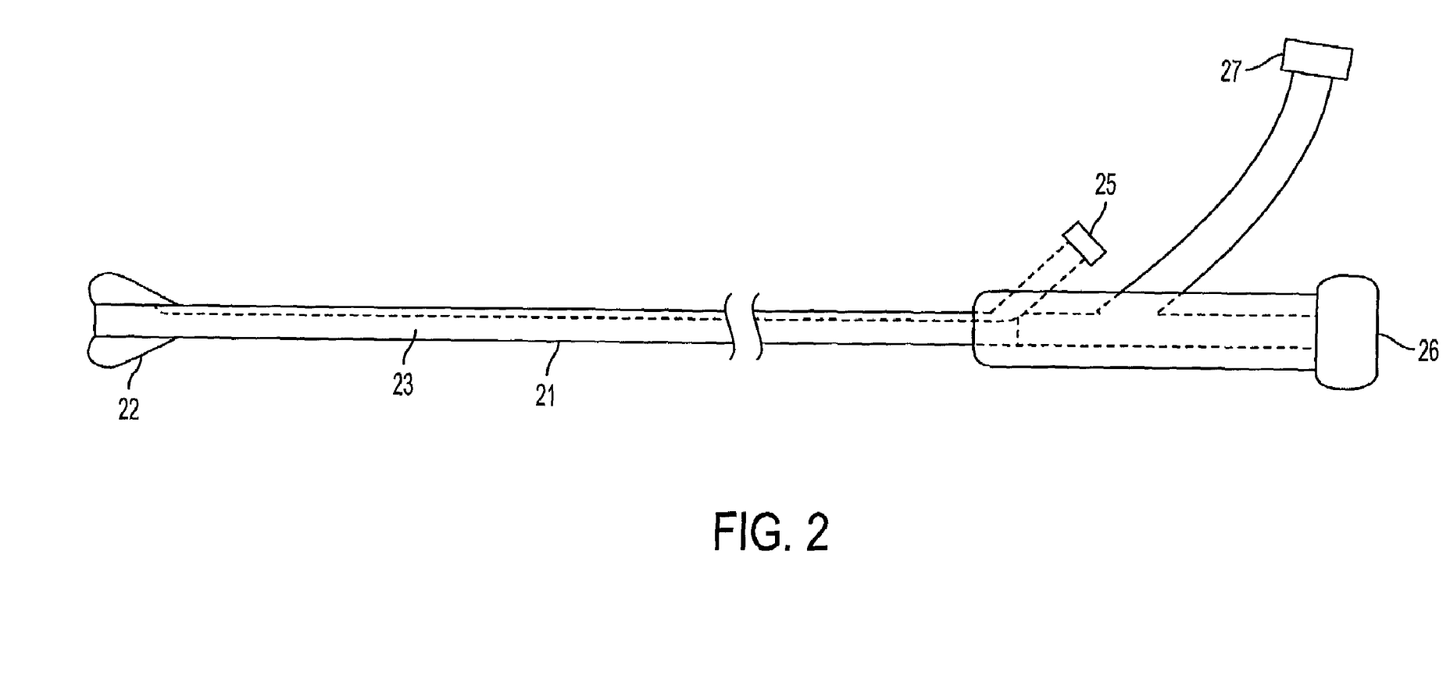
FIG. 2 provides a side view of a catheter apparatus that may be used in conjunction with the blood aspiration system of FIG. 1.

Blood aspiration system 20 may be used in conjunction with a catheter, e.g., as illustrated in FIG. 2 by catheter 21 having proximal and distal ends and working lumen 23 extending therebetween. Catheter 21 preferably is coupled to blood outlet port 27, which is in fluid communication with working lumen 23, inflation port 25, which may be used to inflate occlusion member 22, and hemostatic port 26, which may be used to advance instruments into working lumen 23. In operation, blood outlet port 27 is coupled to blood inlet port 34 of arterial line 30 of FIG. 1 to establish fluid communication between working lumen 23 and lumen 33 of arterial tubing 32.

Lumen 33 of arterial tubing 32 preferably is coupled to inlet tubing 56 of manifold 50 at manifold inlet port 54, as shown from a side sectional view in FIG. 1B. Inlet tubing 56 of manifold 50 also is in fluid communication with suction/infusion port 52, and further is in fluid communication with first check valve 80 and slide valve 100, as described in greater detail hereinbelow.

Manifold outlet port 55 preferably is coupled to threaded cap 75 of filter chamber 70. As described in greater detail hereinbelow, blood flowing into filter chamber 70 from manifold outlet port 55 flows through filter entrance 71 and through filter 72. Filtered blood then exits filter chamber 70 through filter exit port 73, which preferably is coupled to venous line 40. Filter exit port 73 allows for fluid communication between filter chamber 70 and lumen 43 of venous tubing 42. Blood flowing through venous tubing 42 then exits through blood outlet port 44, which may be coupled to a venous return sheath (not shown) that is adapted to be inserted into a patient's venous vasculature. A suitable venous return sheath is described in commonly-assigned U.S. patent application Ser. No. 09/418,727, now U.S. Pat. No. 6,423,032, which is incorporated herein by reference in its entirety.

In accordance with principles of the present invention, blood aspiration system 20 may be used in conjunction with catheter 21 of FIG. 2 during a medical procedure to provide a substantially continuous rate of natural, physiologically-regulated aspiration through working lumen 23.

In particular, catheter 21 may be disposed in a patient's artery and occlusive element 22 may be deployed to occlude flow in the artery. The natural aspiration may be provided through working lumen 23 when a venous return sheath (not shown), which is coupled to blood outlet port 44, is introduced into a remote vein. Once this arterial-venous circuit is established, negative pressure in venous line 40 during diastole will establish a low rate continuous flow of blood through working lumen 23 of catheter 21, to the patient's vein via the venous return line.

Specifically, the arterial-venous circuit allows blood flow in the patient's artery that is distal of occlusive element 22 to flow in a retrograde fashion through working lumen 23 and blood outlet port 27 of FIG. 2, through arterial line 30 and manifold inlet port 54, through slide valve 100 (when slide valve 100 is in an open position), through manifold outlet port 55, filter chamber 70, venous line 40, through the venous return sheath coupled to blood outlet port 44 and back into the remote vein. This method, which utilizes the difference between venous and arterial pressure, may be used to provide a substantially continuous rate of aspiration at a treatment site before, during and after a medical procedure to ensure that emboli generated during the procedure are directed into working lumen 23 for safe removal. Emboli are captured by filter 72 so that filtered blood may be reperfused into the remote vein.

With retrograde flow established in the selected artery via the venous return sheath, a medical procedure may be performed through hemostatic port 26 and working lumen 23 of catheter 21. At any time before, during or after the medical procedure, additional aspiration may be provided at the treatment site via a syringe (not shown) coupled to suction/infusion port 52. It is preferred that the additional suction provided by the syringe only be used in conjunction with the above-described natural aspiration technique for a limited period of time, e.g., at the time a vascular lesion is being traversed or disrupted, to ensure that trauma to the vessel wall due to the external suction is reduced. Alternatively, the syringe may be used to temporarily establish antegrade flow, e.g., to infuse contrast agents, drugs, lytic agents or other therapeutic agents, when slide valve 100 is in a closed position, as described hereinbelow.

In accordance with principles of the present invention, blood aspiration system 20 further comprises pump 60 having housing 61 and plunger 62 disposed within lumen 66 of housing 61, as shown in FIG. 1B. Plunger 62 comprises a proximal end having handle 63, which is configured to be grasped by a physician, and a distal end having tip 64. Plunger 62 is configured so that there is a small amount of friction between an outer surface of plunger 62 and an interior surface of housing 61. The friction holds plunger 62 in place within housing 61 without the need for an external force. However, the small amount of friction may be overcome when an external force is applied, e.g., when plunger 62 is retracted by a physician for purposes described hereinbelow.

Figure 3:
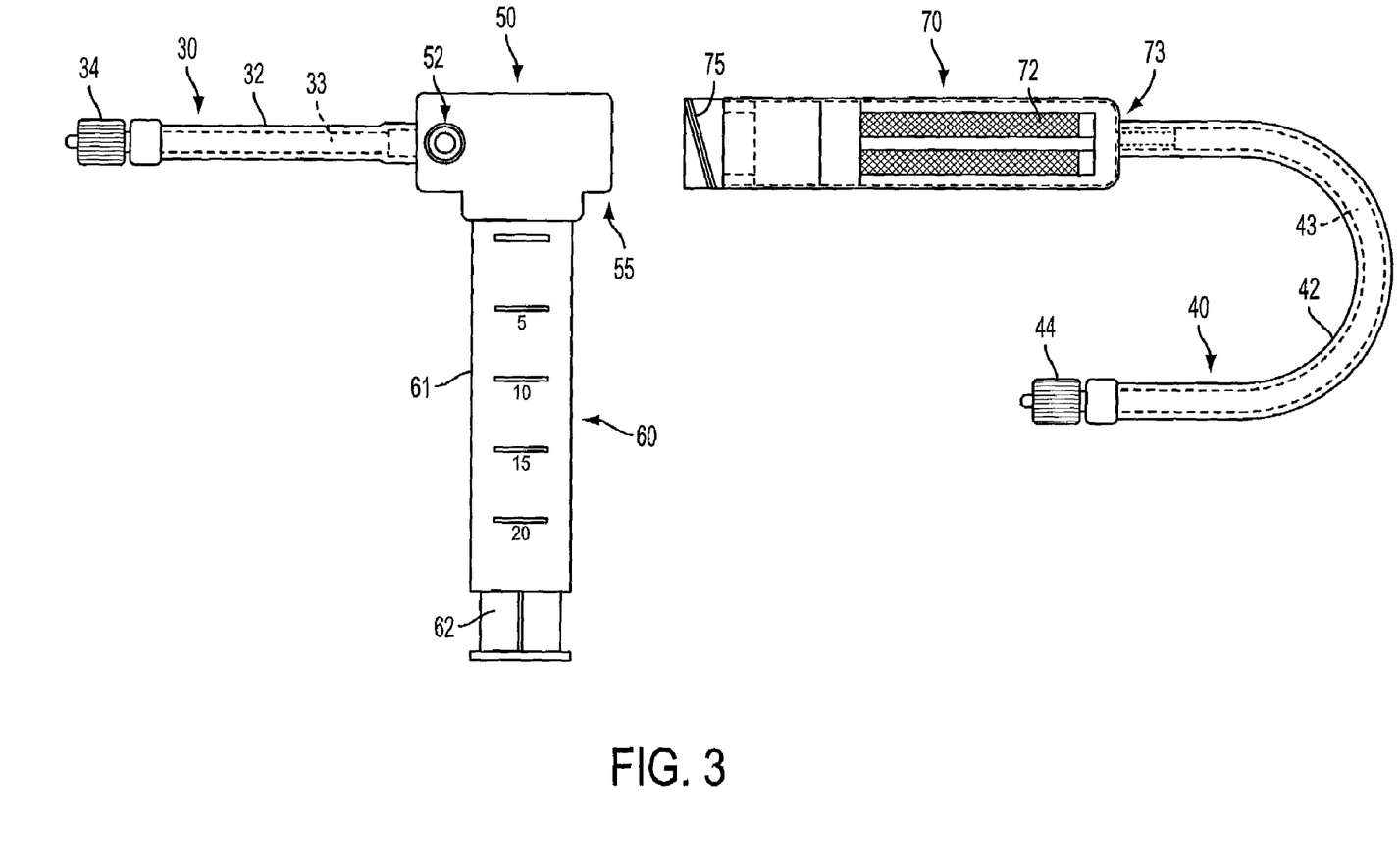
FIG. 3 provides a side view illustrating features of a detachable filter chamber of the present invention.

Referring now to FIG. 3, filter chamber 70 is shown detached from manifold 50 preferably by unscrewing threaded cap 75 from its engagement with a grooved interior section (not shown) of manifold outlet port 55. At this time, emboli captured within filter 72 may be studied and characterized for diagnostic purposes. Filter chamber 70 then may be reattached to manifold 50 by screwing threaded cap 75 into engagement with the grooved interior section of manifold outlet port 55.

Figure 4A:
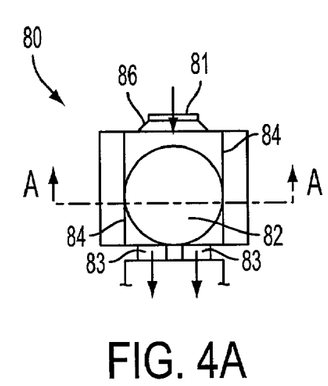
FIGS. 4A-4C are, respectively, side views of a check valve of the present invention in open and closed positions, and a cross-sectional view along line A-A of FIG. 4A.

Referring now to FIG. 4, features of first and second one-way check valves 80 and 90 of FIG. 1B are described. In FIG. 4A, components of first check valve 80 are identical to those provided for second check valve 90, and reference numerals 80-88 that are used to illustratively describe first check valve 80 corresponds to numerals 90-98 that are used to describe the operation of second check valve 90 in FIGS. 6A-6C hereinbelow.

Figure 4B:
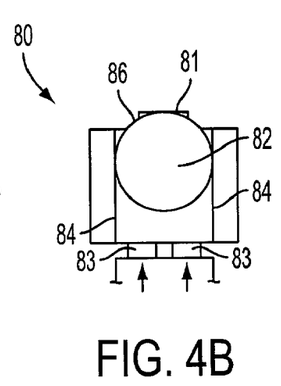
Figure 4C:
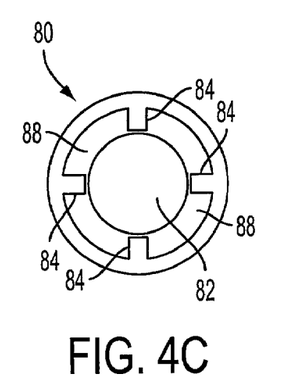

First check valve 80 preferably comprises inlet port 81 having taper 86 disposed at a first end of the valve and exit ports 83 disposed at a second end, as shown in FIG. 4A. First check valve 80 preferably comprises ball 82 that is contained within plurality of ball guides 84, which allow longitudinal movement of ball 82 within the valve. Apertures 88 are formed between ball guides 84, ball 82 and an exterior surface of check valve 80, as shown in a cross-sectional view in FIG. 4C.

First check valve 80 is configured to permit flow through the valve in only one direction, as illustrated by the arrows in FIG. 4A. When flow occurs in this direction, fluid flow passes through inlet port 81 to push ball 82 towards the second end of the valve. With ball 82 at the second end, fluid passes around ball 82, through apertures 88 and out exits ports 83. When flow occurs in the opposite direction, however, ball 82 is configured to prohibit flow from passing through the valve. Specifically, when fluid enters through exit ports 83 in the direction shown in FIG. 4B, ball 82 is pushed toward the first end and plugs against taper 86 and/or inlet port 81 to prohibit flow through inlet port 81. In this manner, first and second check valves 80 and 90 are used, respectively, to prohibit a reversal of flow through manifold inlet port 54 and direct flow in a direction toward manifold outlet port 55 when pump 60 is actuated, as described hereinbelow.

Figure 5A:
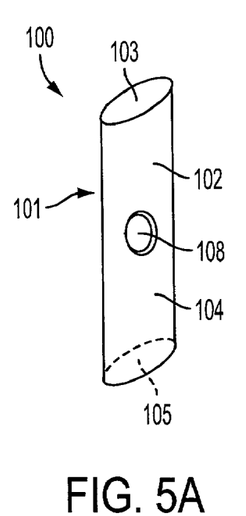
FIGS. 5A-5C are perspective views illustrating slide valves that may be used in accordance with the present invention.

Referring now to FIG. 5, perspective views depicting alternative configurations of slide valve 100 of FIG. 1B are shown. In FIG. 5A, slide valve 100 comprises block 101 having an oval-shaped configuration and first end 103, second end 105, and bore 108 extending laterally though a central region of block 101. Bore 108 is sized to permit blood flow therethrough without imposing significant trauma upon blood vessels. Slide valve 100 further comprises first solid section 102 disposed between first end 103 and bore 108, and second solid section 104 disposed between second end 105 and bore 108.

Figure 6A:
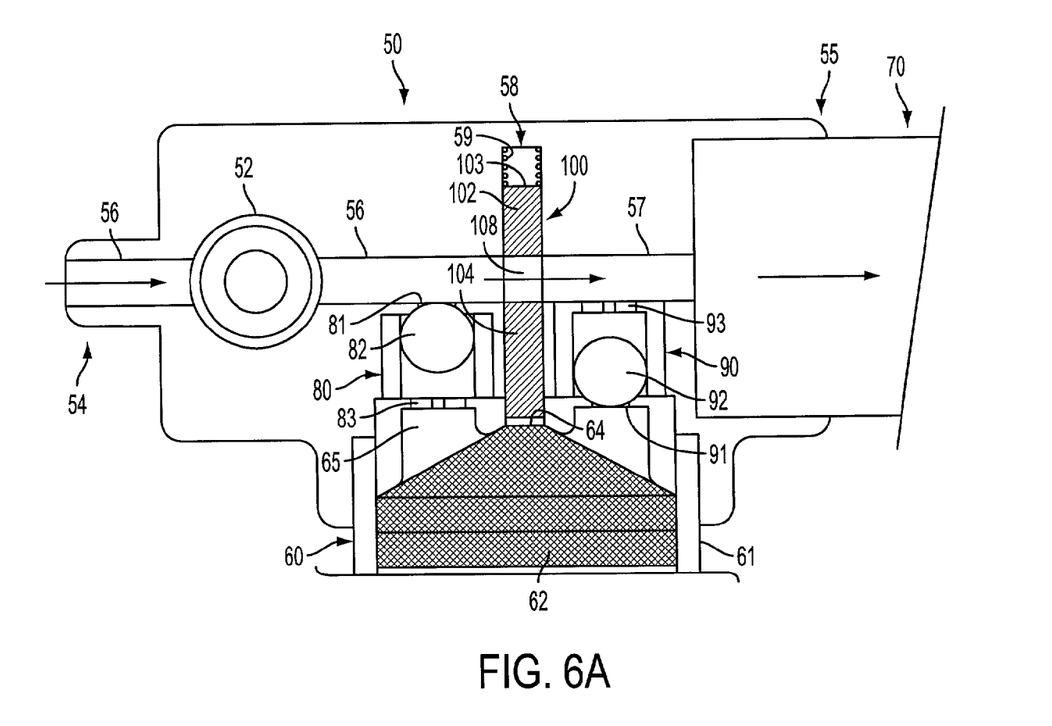
FIGS. 6A-6C describe a preferred method of using the apparatus of FIG. 1 in accordance with the principles of the present invention.
Figure 6B:
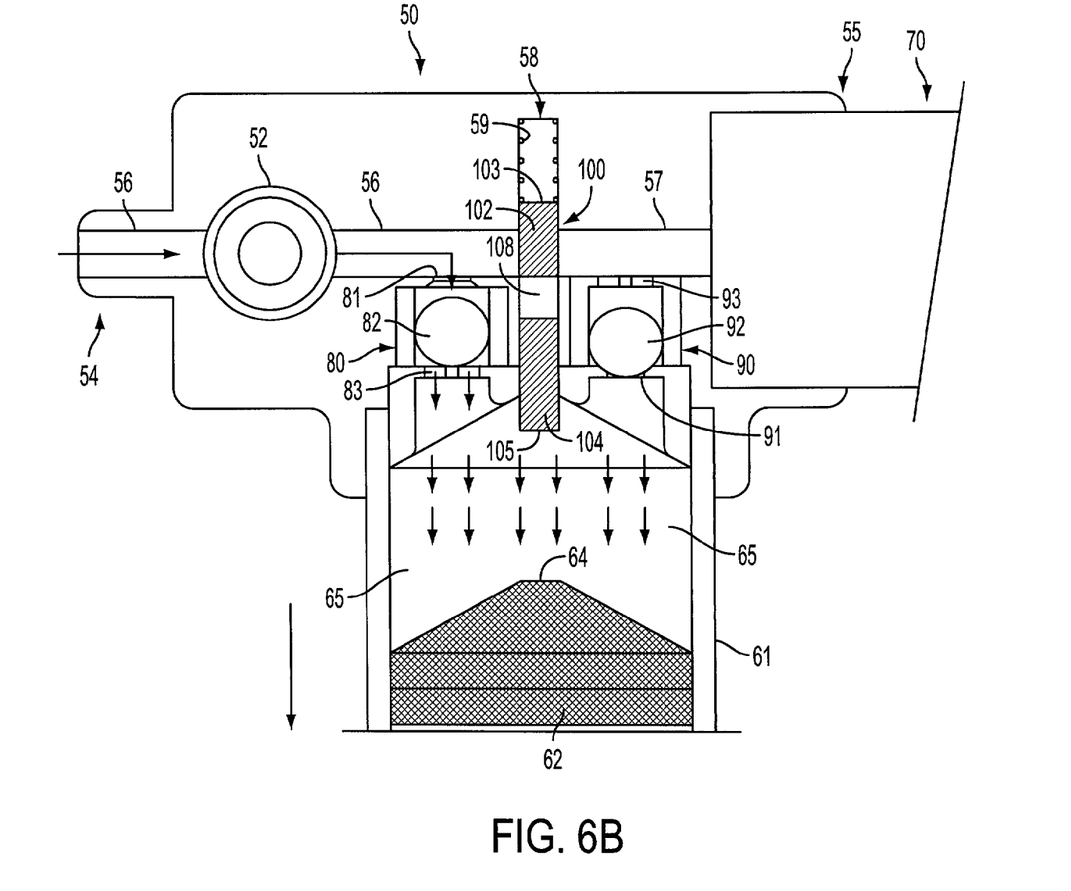
Figure 6C:
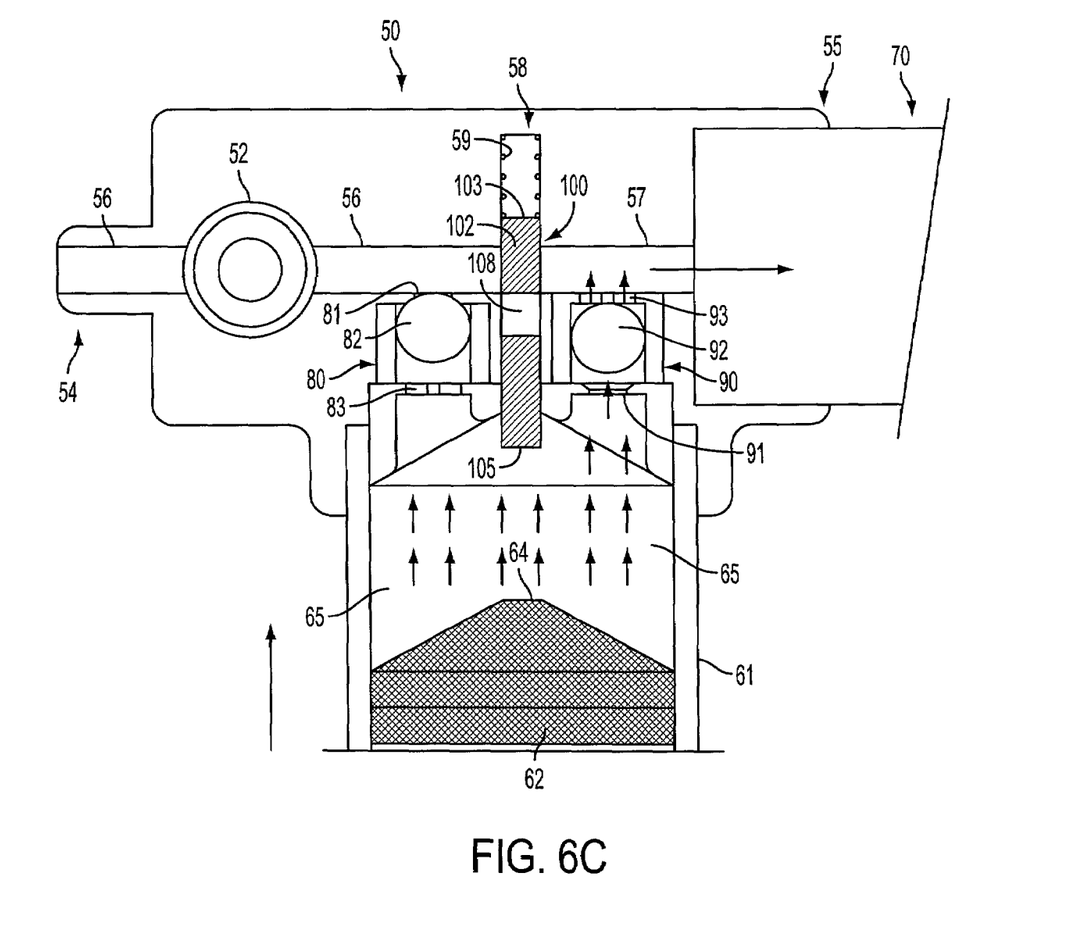

Block 101 of slide valve 100 preferably is disposed within compartment 58 of manifold 50 so that block 101 is configured for longitudinal movement within the compartment. When block 101 comprises an oval-shaped configuration, it is preferred that compartment 58 also comprises an oval configuration to accommodate the block and prevent circumferential rotation of the block within the compartment. As described hereinbelow with respect to FIG. 6, first end 103 is configured to engage a spring disposed within compartment 58, while second end 105 is configured to engage tip 64 of plunger 62.

Figure 5B:
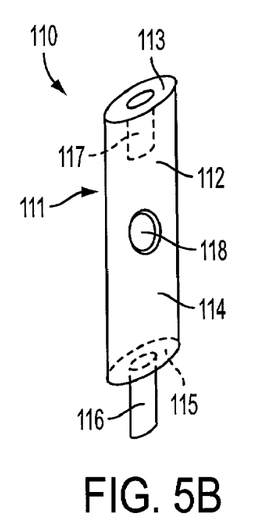

Referring to FIG. 5B, alternative slide valve 110 is shown as comprising block 111 having first end 103, first solid section 112, second solid section 114, second end 115, and bore 118 extending laterally through a central region of block 111. In the embodiment of FIG. 5B, slide valve 110 includes rod 116 that extends longitudinally from second end 116, whereby rod 116 is configured to engage tip 64 of plunger 62. Slide valve 110 further includes bore 117 disposed in first end 113 that extends partially into first solid section 112 of block 111, as shown in FIG. 5B. Bore 117 is configured to receive an end portion of a spring for purposes described hereinafter.

Figure 5C:
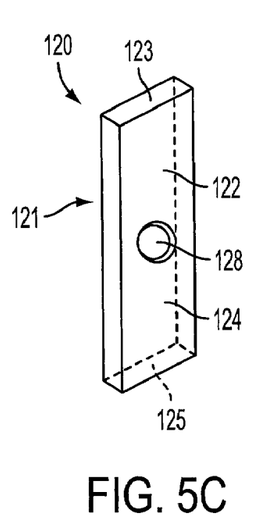

In FIG. 5C, block 121 of alternative slide valve 120 is illustrated as having a rectangular configuration. In this embodiment, rectangular block 121 preferably is configured for longitudinal movement within a rectangular compartment of manifold 50. It will be appreciated by those skilled in the art that, while FIGS. 5A-5C illustrate slide valves having oval and rectangular-shaped configurations, other configurations of the block may be provided to achieve the functions described hereinafter.

Referring now to FIGS. 6A-6C, a preferred method of using apparatus 20 of FIG. 1 to selectively vary the rate of aspiration provided through working lumen 23 of catheter 21 is described. In FIG. 6A, the arrows indicate the direction in which blood flows when natural, physiologically-regulated flow is provided through working lumen 23 when slide valve 100 is provided in an open position.

As described hereinabove, an arterial-venous shunt allows blood flow in the patient's artery that is distal of occlusive element 22 to flow in a retrograde fashion through working lumen 23, through manifold inlet tubing 56, bore 108 and manifold outlet tubing 57, through filter chamber 70 and venous return line 40, and back into a remote vein.

Slide valve 100 is held in the open position, whereby bore 108 is aligned with inlet and outlet tubing 56 and 57 of manifold 50, when plunger 62 is in an advanced position within housing 61, as shown in FIG. 6A. Specifically, plunger 62 is advanced distally so that tip 64 pushes against second end 105 of valve 100 to cause first end 103 to compress spring 59, which is disposed within compartment 58. Wall friction between plunger 62 and an interior wall of housing 61 holds the plunger in the advanced position, i.e., the force of spring 59 cannot overcome the wall friction, so that bore 108 remains aligned with tubing sections 56 and 57.

When slide valve 100 is in the open position shown in FIG. 6A, first and second check valves 80 and 90 are effectively closed. With respect to second check valve 90, blood flowing from outlet tubing 57 into exit ports 93 will push ball 92 against inlet port 91 to close valve 90. With respect to first check valve 80, ball 82 is depicted in a closed position covering inlet port 81 in FIG. 6A. It should be noted that ball 82 actually may be pushed forward by flow from inlet tubing 56, so that small levels of fluid may enter into pump chamber 65. However, so long as plunger 62 remains in the advanced position, flow entering into pump chamber 65 through valve 80 is confined to a small region within pump chamber 65 and, therefore, valve 80 is effectively closed because little or no flow can occur through the valve.

Referring now to FIG. 6B, a physician proximally retracts handle 63 of plunger 62 to draw fluid into pump chamber 65. In a retracted position, tip 64 of plunger 62 no longer contacts second end 105 of slide valve 100. Spring 59 then expands to push block 101 of FIG. 5A in a distal direction and cause first solid segment 102 of valve 100 to block an opening between inlet and outlet tubing 56 and 57. In this closed position, slide valve 100 prohibits fluid entering through manifold inlet port 54 from flowing directly into filter chamber 70.

With slide valve 100 in the closed position, fluid is diverted through first check valve 80. Accordingly, by retracting plunger 62 proximally, fluid may be aspirated from a blood vessel through working lumen 23 of catheter 21 and diverted into pump chamber 65. The rate of aspiration in the vessel may be controlled by proximally retracting plunger 62 a known distance within housing 61 using indicia 69 disposed on housing 61, as shown in FIG. 1A.

Referring now to FIG. 6C, plunger 62 is advanced distally by a physician to cause fluid in pump chamber 65 to be forced through second check valve 90. Specifically, when plunger 62 is advanced distally, fluid flow pushes ball 92 of valve 90 in a distal direction, i.e., away from inlet port 91, to permit fluid flow through exit ports 93 of valve 90. Fluid then flows through outlet tubing 57 into filter chamber 70, through filter 72, through venous line 40, and through a venous return sheath (not shown) into a remote vein. This technique advantageously allows filtered blood to be reperfused directly into a patient's body. When plunger 62 is advanced distally, first check valve 80 is forced into a closed position because ball 82 is pushed against inlet port 81.

In accordance with principles of the present invention, the use of two opposing check valves 80 and 90 ensures that fluid is directed through manifold 50 exclusively in one direction when pump 60 is actuated, i.e., fluid may flow from inlet tubing 56 into pump chamber 65 and then may flow into outlet tubing 57. However, fluid may not flow in a reverse direction from pump chamber 65 back towards catheter 21 because first check valve 80 will close. Similarly, fluid from filter chamber 70 may not flow in a reverse direction into pump chamber 65 because second check valve 90 will close. It should be noted that slide valve 100 will remain in the closed position when pump 60 is actuated so long as plunger 62 is not fully advanced to cause tip 64 to engage second end 105 of valve 100.

Using the techniques described hereinabove, it is possible to achieve variable rates of aspiration through working lumen 23 of catheter 21 using pump 60. In operation, a physician selectively may retract and advance plunger 62 a desired amount, using markings 69, for as many cycles as desired. This allows a physician to achieve selectively higher rates of aspiration in a vessel at a location distal of occlusion element 22 without the need for an external suction device. However, if desired, suction-assisted aspiration and/or infusion may be applied through suction/infusion port 52 when slide valve 100 is in a closed position, as described hereinabove.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

The invention claimed is:

1. Apparatus suitable for providing variable rates of aspiration to a working lumen of a catheter, the apparatus comprising:
   a manifold having an inlet port, an outlet port, a slide valve slidingly disposed therebetween, the slide valve having an open position and a closed position, and a first check valve disposed within the manifold and in fluid communication with the inlet port, wherein the inlet port is in fluid communication with the working lumen of the catheter;
   a pump coupled to the manifold, the pump having a housing defining a pump lumen and a plunger disposed within the lumen, the pump coupled to the manifold so that the plunger contacts and retains the slide valve in the open position when the plunger is fully depressed in the pump lumen;
   a spring in operative association with the slide valve to bias the slide valve to a closed position:
   wherein proximally retracting the plunger moves the slide valve to the closed position and causes fluid to enter the pump lumen, whereby proximally retracting the plunger varies the rate of aspiration in the working lumen of the catheter, and wherein distally advancing the plunger causes fluid in the pump lumen to exit through the outlet port.

2. The apparatus of claim 1 wherein the outlet port is coupled to a venous line that is in fluid communication with a patient's venous vasculature.

3. The apparatus of claim 1 further comprising a filter chamber having a filter disposed therein coupled to the outlet port of the manifold.

4. The apparatus of claim 3 wherein the filter chamber is detachable from the outlet port.

5. The apparatus of claim 1 wherein distally advancing the plunger compresses the slide valve against the spring.

6. The apparatus of claim 5 wherein the slide valve further comprises a block having a first end, a second end, and a bore extending laterally through a central region of the block.

7. The apparatus of claim 6 wherein the block comprises an oval-shaped configuration.

8. The apparatus of claim 6 wherein the block comprises a rectangular-shaped configuration.

9. The apparatus of claim 1 wherein the manifold further comprises a suction/infusion port in fluid communication with the working lumen of the catheter.

10. The apparatus of claim 1 wherein the housing further comprises a plurality of indicia for quantifying a rate of pump-assisted aspiration.

11. The apparatus of claim 1 wherein the first check valve is configured to permit fluid flow from the inlet port into a pump chamber of the housing.

12. The apparatus of claim 11 wherein the first check valve is configured to close when the plunger is advanced in a distal direction.

13. The apparatus of claim 1 further comprising a second check valve disposed within the manifold that is configured to permit fluid flow in a direction from a pump chamber of the housing towards the outlet port.

14. The apparatus of claim 13 wherein the second check valve is configured to close when the plunger is retracted in a proximal direction.

15. Method for providing variable rates of aspiration to a working lumen of a catheter, the method comprising:
providing apparatus comprising a manifold having an inlet port in fluid communication with the working lumen of the catheter, an outlet port, a slide valve slidingly disposed therebetween and operable between an open position and a closed position, a spring in operative association with the slide valve to bias the slide valve to the closed position, and a first check valve disposed within the manifold and in fluid communication with the inlet port, the apparatus further comprising a pump coupled to the manifold, the pump including a housing having a pump lumen and a plunger disposed within the pump lumen, the pump coupled to the manifold so that the plunger contacts and retains the slide valve in the open position when the plunger is fully depressed in the pump lumen;
proximally retracting the plunger to move the slide valve to the closed position and to cause fluid to enter the pump lumen, whereby proximally retracting the plunger causes the spring to urge the slide valve to the closed position and varies the rate of aspiration in the working lumen of the catheter; and
distally advancing the plunger to cause fluid in the pump lumen to exit through the outlet port.

16. The method of claim 15 further comprising actuating the first check valve to allow flow from the inlet port into the pump lumen when the plunger is proximally retracted.

17. The method of claim 16 further comprising causing the first check valve to close when the plunger is distally advanced.

18. The method of claim 15 further comprising providing a second check valve disposed between the pump lumen and the outlet port, and actuating the second check valve to open to allow flow from the pump lumen into the outlet port when the plunger is distally advanced.

19. The method of claim 18 further comprising causing the second check valve to close when the plunger is proximally retracted.

20. The method of claim 15 wherein distally advancing the plunger compresses the slide valve against the spring.

21. The method of claim 15 further comprising reperfusing blood that exits through the outlet port into a remote vein.

22. The method of claim 15 further comprising:
providing a filter chamber coupled to the outlet port of the manifold, the filter chamber having a filter disposed therein; and
filtering blood flowing from the outlet port through the filter chamber.

23. The method of claim 22 further comprising selectively detaching the filter chamber from engagement with the outlet port.

24. The method of claim 15 further comprising selectively providing suction-assisted aspiration through the working lumen of the catheter through a suction/infusion port coupled to the manifold.

* * * * *